(12) United States Patent
Fukuda

(10) Patent No.: US 9,629,531 B2
(45) Date of Patent: Apr. 25, 2017

(54) DISTAL END CONFIGURING MEMBER OF MEDICAL INSTRUMENT, ENDOSCOPE CLEANING SHEATH AND ENDOSCOPE SYSTEM USING THE ENDOSCOPE CLEANING SHEATH

(71) Applicant: OLYMPUS CORPORATION, Tokyo (JP)

(72) Inventor: Yusuke Fukuda, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 142 days.

(21) Appl. No.: 14/644,357

(22) Filed: Mar. 11, 2015

(65) Prior Publication Data

US 2015/0182108 A1 Jul. 2, 2015

Related U.S. Application Data

(63) Continuation of application No. PCT/JP2014/059763, filed on Apr. 2, 2014.

(30) Foreign Application Priority Data

May 23, 2013 (JP) .................................. 2013-109116

(51) Int. Cl.
*A61B 1/00* (2006.01)
*A61B 1/12* (2006.01)
(Continued)

(52) U.S. Cl.
CPC .......... *A61B 1/126* (2013.01); *A61B 1/00091* (2013.01); *A61B 1/00128* (2013.01); *A61B 1/00135* (2013.01); *G02B 23/2476* (2013.01)

(58) Field of Classification Search
CPC . A61B 1/126; A61B 1/00128; A61B 1/00135; A61B 1/00089; A61B 1/00091; A61B 1/00119; G02B 23/2476
(Continued)

(56) References Cited

U.S. PATENT DOCUMENTS 5,575,756 A 11/1996 Karasawa et al.
5,746,695 A * 5/1998 Yasui ................. A61B 1/00091
600/121
(Continued)

FOREIGN PATENT DOCUMENTS

JP 06-027393 A 2/1994
JP 07-275185 A 10/1995
(Continued)

OTHER PUBLICATIONS

International Search Report dated Jul. 15, 2014 issued in PCT/JP2014/059763.

*Primary Examiner* — Timothy J Neal
(74) *Attorney, Agent, or Firm* — Scully, Scott, Murphy & Presser, P.C.

(57) ABSTRACT

The invention is formed by including a proximal end portion having an inside diameter capable of receiving a member having a shape including a substantially circular outer circumferential portion and a convex portion formed at the outer circumferential portion as an outside diameter shape, and having an outside diameter formed into a shape substantially similar to the outer circumferential shape, a distal end portion in a substantially cylindrical shape having an outside diameter that is equal to or larger than a maximum outside diameter of the proximal end portion, and a cutout portion that is formed in a site corresponding to the convex portion, and is in a shape which is cut out from the proximal end portion to the distal end portion.

7 Claims, 10 Drawing Sheets

(51) Int. Cl.
*G02B 23/24* (2006.01)
*A61B 1/04* (2006.01)

(58) Field of Classification Search
USPC .................................. 600/121, 127, 129
See application file for complete search history.

(56) References Cited

U.S. PATENT DOCUMENTS

2004/0073088 A1   4/2004  Friedman et al.
2006/0074274 A1   4/2006  Friedman et al.
2008/0188715 A1*  8/2008  Fujimoto ........... A61B 1/00091
                                                      600/157

FOREIGN PATENT DOCUMENTS

| JP | 2006-507861 A | 3/2006 |
| JP | 2006-136671 A | 6/2006 |
| JP | 2008-132282 A | 6/2008 |
| WO | WO 2004/034875 A2 | 4/2004 |

* cited by examiner

DISTAL END CONFIGURING MEMBER OF MEDICAL INSTRUMENT, ENDOSCOPE CLEANING SHEATH AND ENDOSCOPE SYSTEM USING THE ENDOSCOPE CLEANING SHEATH

CROSS REFERENCE TO RELATED APPLICATION

This application is a continuation application of PCT/JP2014/059763 filed on Apr. 2, 2014 and claims benefit of Japanese Application No. 2013-109116 filed in Japan on May 23, 2013, the entire contents of which are incorporated herein by this reference.

BACKGROUND OF THE INVENTION

1. Field of the Invention

The invention relates to a distal end configuring member of a medical instrument such as an endoscope cleaning sheath including a configuration that sprays an atomized mixed fluid toward front surfaces of an observation window, an illuminating window and the like that are provided on a distal end face of an insertion portion or the like of an endoscope, and removes adherents adhering to surfaces of the respective windows, an endoscope cleaning sheath and an endoscope system using the endoscope cleaning sheath.

2. Description of the Related Art

In recent years, endoscope systems in a medical field have been widely put to practical use with the objective of minimal invasiveness on the occasion of in-vivo observation, medical treatment, surgical operations and the like, and have been widely used in laparoscopic surgical operations that perform therapeutic treatment without performing abdominal section, for example.

For example, in a laparoscopic surgical operation, a trocar is punctured into an abdominal region of a patient, and an endoscope for observation is introduced into the body with use of the trocar. At this time, during in-vivo observation by the endoscope, mucus, blood, fat, filth and the like (hereinafter, these matters will be simply called adherents and the like) sometimes adhere to outer surfaces at the front surface sides of the observation window, the illuminating window and the like which are provided at the distal end face of the insertion portion or the like of the endoscope, and these adherents and the like sometimes hinder favorable observation.

Therefore, in the conventional endoscope systems and the like of this kind, various medical instruments such as an endoscope cleaning sheath for removing adherents and the like on the outer surfaces of the observation windows and the illuminating windows on the insertion portion distal end faces are proposed by, for example, Japanese Patent Application Laid-Open Publication No. 2008-132282.

The endoscope cleaning sheath which is disclosed by Japanese Patent Application Laid-Open Publication No. 2008-132282 described above is of a mode including a wiper unit that removes the adherents on an observation window and an illuminating window. In the endoscope cleaning sheath described in the publication, the configuration having a multi lumen tube that is formed into a tube shape in which an endoscope insertion portion is insertable, and having protruded portions on an outer circumferential face, and a distal end configuring member fixable to a distal end portion of the multi lumen tube is described.

Further, in the conventional endoscope cleaning sheaths, various sheaths in which spray nozzles that eject a mixed liquid prepared by mixing a gas and a liquid and atomized are provided at distal end configuring members are proposed, for example, for the purpose of cleaning the adherents and the like on the outer surfaces of the observation windows and the like of endoscopes and the like which are fitted.

In the conventional endoscope cleaning sheath of this kind, a sheath insertion portion is formed of a flexible tube having flexibility in order to be compatible with an endoscope with a distal end portion configured to be bendable, and a distal end configuring member having a spray nozzle is generally formed from a rigid resin, a metal member or the like. Further, as the flexible tube for use in the sheath insertion portion, a multi lumen tube is adopted, which is provided with a main lumen for allowing an endoscope to be inserted through, and at least two sub lumens for performing gas feeding, liquid feeding and the like. Here, the sectional shape of the multi lumen tube is sometimes formed into such a deformed shape as a shape in which sites where the above described sub lumens are provided to protrude radially, for example, instead of a circular shape. In such a case, the sectional shape of an inner circumferential face of the distal end configuring member to which the multi lumen tube is integrally joined is also formed into a substantially similar deformed shape in accordance with the sectional shape of the multi lumen tube. Like this, in the medical instruments such as an endoscope cleaning sheath, various medical instruments are present, which have the modes in which the distal end configuring members and flexible tubes are joined.

SUMMARY OF THE INVENTION

A distal end configuring member of a medical instrument of one aspect of the present invention is formed by including a proximal end portion having an inside diameter capable of receiving a member having a shape including a substantially circular outer circumferential portion and a convex portion formed at the outer circumferential portion shape as an outer circumferential shape, and having an outside diameter formed into a shape substantially similar to the outer circumferential shape, a distal end portion in a substantially cylindrical shape having an outside diameter that is equal to or larger than a maximum outside diameter of the proximal end portion, and a cutout portion that is formed in a site corresponding to the convex portion, and is in a shape which is cut out from the proximal end portion to the distal end portion.

An endoscope cleaning sheath of one aspect of the present invention includes the distal end configuring member of the medical instrument, wherein the distal end configuring member further has a spray nozzle that sprays an atomized mixed liquid of a gas and a liquid.

Further, an endoscope system of one aspect of the present invention is an endoscope system including an endoscope and a light source apparatus, and is configured by including an endoscope cleaning sheath including a tube-shaped insertion portion having a shape including a substantially circular outer circumferential portion and a convex portion formed at the outer circumferential portion, as an outside diameter outer circumferential shape, and a distal end configuring member formed by including a proximal end portion having an inside diameter capable of receiving the tube-shaped insertion portion, and having an outside diameter formed into a shape substantially similar to the outer circumferential shape, a distal end portion in a substantially circular shape having an outside diameter equal to or larger than a maximum outside diameter of the proximal end portion, a cutout portion that is formed in a site corresponding to the convex portion and is in a shape which is cut out from the proximal end portion to the distal end portion, and a spray nozzle that sprays an atomized mixed liquid of a gas and a liquid, and a tubular member through which the endoscope cleaning sheath is inserted.

DETAILED DESCRIPTION OF THE PREFERRED EMBODIMENTS

Figure 1:
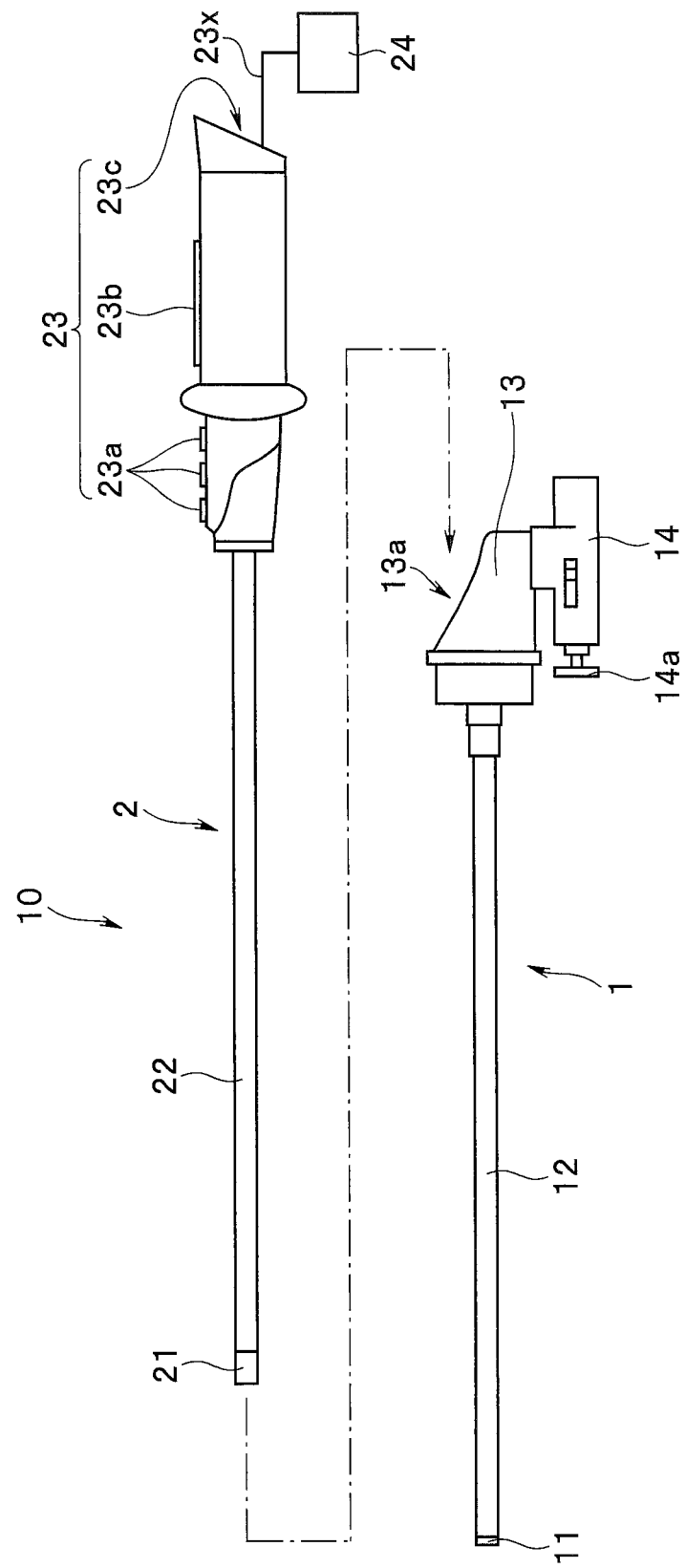
FIG. 1 is a schematic configuration diagram showing an endoscope cleaning sheath including a distal end configuring member of a first embodiment of the present invention, and an endoscope for use in combination with the endoscope cleaning sheath.

Hereinafter, the present invention will be described in accordance with an illustrated embodiment.

One embodiment that will be described as follows exemplifies an endoscope cleaning sheath of a mode including an insertion portion in a tube shape in which an insertion portion of an endoscope can be inserted, and a distal end configuring member that is joined to a distal end of the insertion portion, wherein the distal end configuring member includes a spray nozzle for cleaning adherents and the like on front surface side outer surfaces of an observation window, an illuminating window and the like of an endoscope or the like which is inserted through the above described tube-shaped insertion portion, for example, as a medical instrument to which the distal end configuring member of the present invention is applied, and an endoscope system using the endoscope cleaning sheath.

Note that in respective drawings for use in the following explanation, respective components are sometimes shown with a scale made to differ at each of the respective components, in order to make the respective components have such sizes as to be recognizable on the drawings. Accordingly, in the present invention, numbers and quantities of the components, shapes of the components, ratios of the sizes of the components, and relative positional relationships of the respective components which are illustrated in the drawings are not limited only to the illustrated modes.

Respective schematic configurations of the endoscope cleaning sheath including the distal end configuring member of one embodiment of the present invention, and the endoscope system including an endoscope that is used by being combined with the endoscope cleaning sheath will be described as follows with use of FIG. 1.

First, the schematic configuration of the endoscope system including the endoscope which is used by being combined with the above described endoscope cleaning sheath including the distal end configuring member of the present embodiment will be described with use of FIG. 1. Note that the endoscope system described in the present embodiment refers to a system including a trocar (see FIG. 11 and the like) that is a tubular member and will be described later, a light source apparatus 24 and the like, in addition to the endoscope cleaning sheath as the medical instrument including the distal end configuring member of the present embodiment, and the endoscope which is used by being combined with the endoscope cleaning sheath.

An endoscope 2 that is included in an endoscope system 10 of the present invention is a so-called optical endoscope that is configured mainly by an endoscope distal end portion 21, an endoscope insertion portion 22, an eyepiece portion 23 and the like, and a basic configuration thereof is substantially similar to the configurations of optical endoscopes which have been conventionally put to practical use generally. Accordingly, explanation of the configuration will be limited to describing only an outline as follows.

The endoscope distal end portion 21 of the above described endoscope 2 has a photographing optical system, an illuminating optical system and the like therein, and an observation window, an illuminating window and the like are placed on a distal end face thereof, though not illustrated. An image guide bundle is connectively provided at the above described photographing optical system, and a light guide bundle is connectively provided at the illumination optical system. The image guide bundle and the light guide bundle are inserted and disposed from a distal end side to a proximal end side inside the endoscope insertion portion 22, that is, inserted and disposed from an inside of the above described endoscope distal end portion 21 at the distal end side and to an inside of the above described eyepiece portion 23 at the proximal end side. Further, the above described light guide bundle further passes through the eyepiece portion 23, extends to a light source apparatus 24 (see FIG. 1) via a cable 23x (see FIG. 1) that is connected to the eyepiece portion 23, and is connected to the light source apparatus 24. By the configuration, the light guide bundle transmits illuminating light that is emitted from the above described light source apparatus to the above described illumination optical system, and irradiates the illuminating light toward a front from the above described illuminating window. The above described image guide bundle transmits an optical image that is formed by the above described photographing optical system to the above described eyepiece portion 23.

A mode of the endoscope 2 which is used in the present embodiment is described as the mode of the optical endoscope as described above, but the mode of the endoscope for use in the endoscope cleaning sheath including the distal end configuring member of the present embodiment is not limited to the optical endoscope. The mode of the endoscope for use in the endoscope cleaning sheath including the distal end configuring member of the present embodiment may be a mode of a so-called electronic endoscope, besides the above described optical endoscope.

A configuration of the electronic endoscope is as follows, for example (illustration is omitted; note that refer to FIG. 1 for a schematic configuration thereof). That is to say, the electronic endoscope is configured by including an image pickup unit including an image pickup optical system, an image pickup device and the like inside the endoscope distal end portion 21, for example, and having an observation window, an illuminating window and the like on a distal end face of the above described endoscope distal end portion 21. The distal end side of the endoscope insertion portion 22 is provided connectively to the proximal end side of the endoscope distal end portion 21. Further, a distal end side of an operation portion (a site corresponding to the eyepiece portion 23) is provided connectively to a proximal end side of the endoscope insertion portion 22. Various operation members are placed on an outer surface of the operation portion. Further, a universal cord is extended from the operation portion, and the universal cord is connected to the light source apparatus and a video processor (not illustrated; an outside apparatus corresponding to a reference sign 24 in FIG. 1) and the like. An electronic endoscope of the configuration as above is of a general configuration. Furthermore, the configuration of the above described endoscope insertion portion may be a flexible configuration configured to be bendable, or may be a rigid configuration.

Next, a detailed configuration of the endoscope cleaning sheath including the distal end configuring member of the present embodiment will be described with use of FIG. 1 to FIG. 10.

A schematic configuration of an endoscope cleaning sheath 1 is configured mainly by a distal end configuring member 11, a tube-shaped insertion portion 12, an operation portion 13, a control switch portion 14 and the like, as shown in FIG. 1. Here, the distal end configuring member 11 has an inside diameter capable of receiving a distal end portion of the tube-shaped insertion portion 12, has a distal end portion of the tube-shaped insertion portion 12 connected to an inside diameter at a proximal end side of the distal end configuring member 11, and jointed to be integrated therewith. A whole of the distal end configuring member 11 is formed into a substantially cylindrical shape by a rigid member such as a rigid resin or a metal member.

The tube-shaped insertion portion 12 has the distal end configuring member 11 joined to a distal end side, as described above, and has the operation portion 13 connected to a proximal end side to be integrated therewith. The tube-shaped insertion portion 12 is formed by having a plurality of conduits which allow the above described endoscope insertion portion 22 to pass through, and allow a gas and a fluid for ejecting an atomized mixed liquid from an ejection port 11 as (details will be described later; refer to FIG. 2 and the like) of a spray nozzle 11*a* of the distal end configuring member 11. For this purpose, the tube-shaped insertion portion 12 is configured by a so-called multi lumen tube that is formed into a tube shape by using a flexible material as a whole, and has a plurality of conduits.

Figure 3:
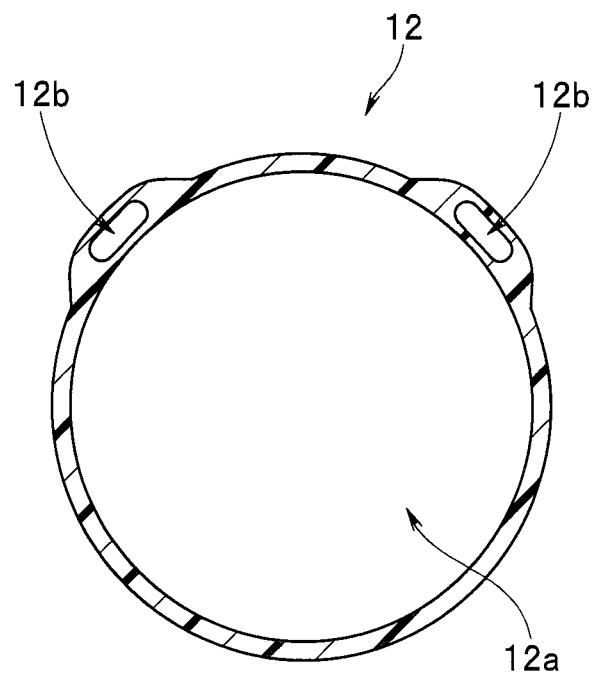
FIG. 3 is a sectional view (seen from an arrow [3] direction in FIG. 2) of a tube-shaped insertion portion in the endoscope cleaning sheath in FIG. 1.

Here, a configuration of the tube-shaped insertion portion 12 will be described in detail. A sectional shape of the tube-shaped insertion portion 12 is formed as shown in FIG. 3, for example. The tube-shaped insertion portion 12 is formed by having one main lumen 12*a* to be a main conduit through which the above described endoscope insertion portion 22 is inserted, and a plurality (two in the present embodiment) of sub lumens 12*b* that are formed at sites near an outer circumference of the main lumen 12*a*. One of the above described two sub lumens 12*b* is a gas feeding conduit through which a gas is passed, and the other one is a liquid feeding conduit through which a liquid such as water is passed.

Note that as shown in FIG. 3, the sectional shape of the tube-shaped insertion portion 12 is formed in such a manner that portions where the two sub lumens 12*b* are formed slightly protrude outward in a radial direction. That is to say, the above described tube-shaped insertion portion 12 is formed of an outside diameter outer circumferential shape formed by having an outer circumferential portion with a substantially circular section as a whole, and having a plurality of convex portions at part of the outer circumferential portion.

Here, the tube-shaped insertion portion 12 itself is formed by using a flexible material as described above, and therefore, when an external force is applied to sites (the above described convex portions) where the above described sub lumens 12*b* are formed, for example, from an outer surface, the respective conduits formed by the sub lumens 12*b* are displaced into crushed modes, but the sectional shape of the tube-shaped insertion portion 12 keeps a shape close to a substantially circular shape as a whole. That is to say, the tube-shaped insertion portion 12 has flexibility so that no problem arises even if the respective conduits are in crushed forms at this time.

Further, a wall thickness of the tube-shaped insertion portion 12 is formed to be substantially uniform throughout an entire circumference including the protruded portions where the above described two sub lumens 12*b* are formed, and to have thin thickness as a whole. The sectional shape as above is adopted, whereby a bending load that is applied to the tube-shaped insertion portion 12, for example, can be reduced. Accordingly, durability of the endoscope cleaning sheath 1 can be improved by adoption of the tube-shaped insertion portion 12 with the sectional shape as above.

To the operation portion 13, the proximal end side of the above described tube-shaped insertion portion 12 is connected as described above. In the operation portion 13, an opening 13*a* (see FIG. 1) for inserting the above described endoscope insertion portion 22 into the main lumen 12*a* of the tube-shaped insertion portion 12 is formed. The opening 13*a* is formed to connect to the main lumen 12*a* of the tube-shaped insertion portion 12 which is connected to the operation portion 13.

The control switch portion 14 is formed integrally with the above described operation portion 13, and is configured by including an operation switch 14*a* that controls a gas feeding operation and a spray operation, and the like. A gas feeding tube and a liquid feeding tube that are extended from a gas feeding and liquid feeding apparatus not illustrated are connected to the control switch portion 14. The gas feeding tube and the liquid feeding tube are connected to the respective two sub lumens 12b of the above described tube-shaped insertion portion 12 via the above described operation switch 14a inside the above described control switch portion 14.

The above described operation switch 14a is configured by a two-stage switch, for example, and executes a gas feeding action by a pressing operation at a first stage, for example. When a depressing operation (a pressing operation at a second stage) is further performed from the above state (the pressing operation state at the first stage), a liquid feeding action is executed in addition to the gas feeding action. Thereby, an atomized mixed liquid is sprayed from the ejection port 11aa of the spray nozzle 11a of the distal end configuring member 11. Note that details of an action by an operation of the endoscope cleaning sheath 1 will be described later.

Figure 2:
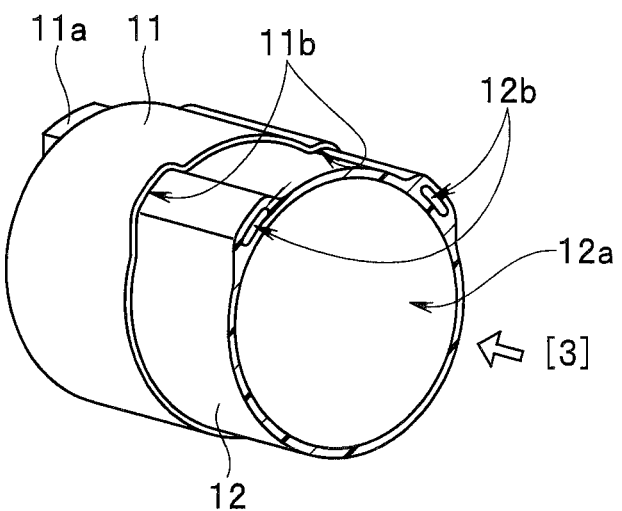
FIG. 2 is an essential part enlarged perspective view enlarging and showing a distal end site of the endoscope cleaning sheath in FIG. 1.
Figure 4:
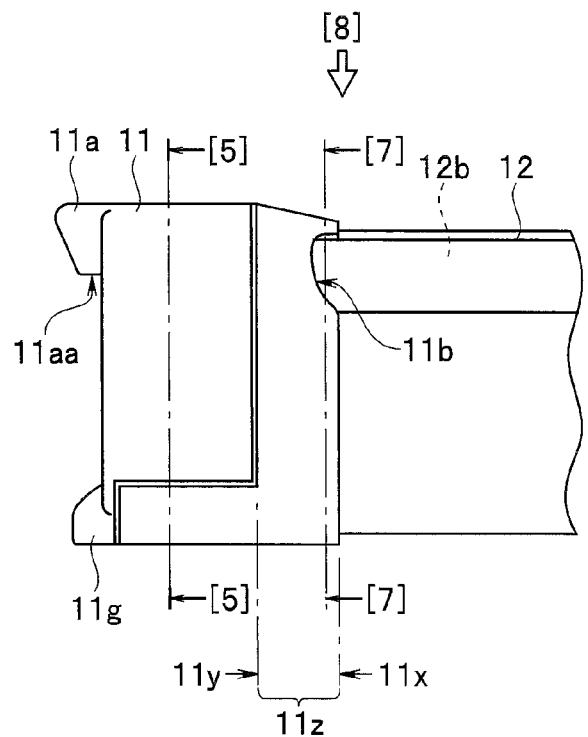
FIG. 4 is an essential part enlarged side view enlarging and showing the distal end site of the endoscope cleaning sheath in FIG. 1.

On a front surface side of the distal end configuring member 11 in the above described endoscope cleaning sheath 1, the spray nozzle 11a for ejecting the mixed liquid which is atomized to clean the adherents and the like adhering to the front surface side outer surfaces of the observation window, the illuminating window and the like (not illustrated) on the distal end face of the above described endoscope 2 which is inserted through and disposed in the above described tube-shaped insertion portion 12 is integrally placed as shown in FIG. 2, FIG. 4 and the like.

Therefore, in the distal end configuring member 11, channels (see reference signs 11c and 11d in FIG. 5, FIG. 8 and the like) are formed, which mix and atomize the gas and the liquid which flow via the two sub lumens 12b of the above described tube-shaped insertion portion 12, and thereafter cause the atomized mixture to flow to the spray nozzle 11a.

Here, the channels (11c, 11d) which are formed inside the distal end configuring member 11 are formed as follows (see FIG. 5, FIG. 8 and the like). That is to say, the channel 11c is formed in a site where the plurality (two) of sub lumens 12b of the tube-shaped insertion portion 12 which is joined to the distal end configuring member 11 are respectively connected, and is a channel for the gas and the liquid that are fed out from the above described gas feeding and liquid feeding apparatus (not illustrated) via the respective sub lumens 12b to flow separately respectively.

Figure 5:
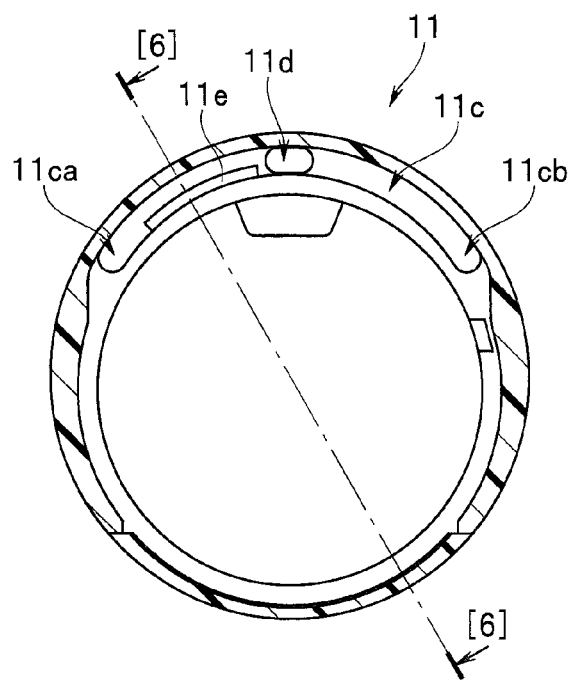
FIG. 5 is a sectional view (taken along a line [5]-[5] in FIG. 4) of the distal end configuring member in the endoscope cleaning sheath in FIG. 1.
Figure 6:
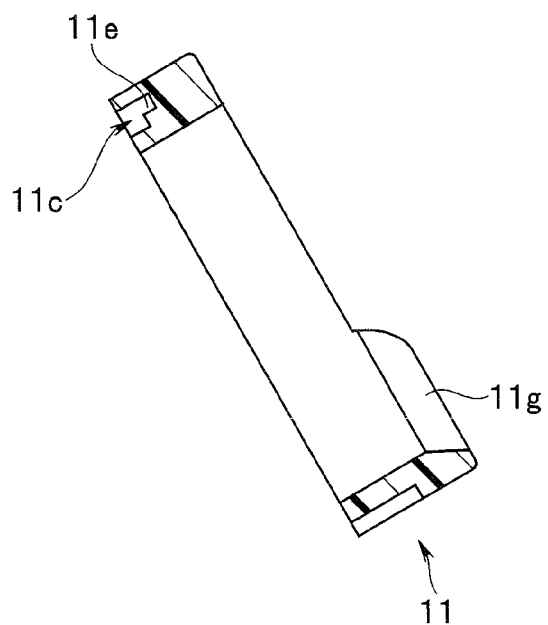
FIG. 6 is a sectional view taken along a line [6]-[6] in FIG. 5.
Figure 7:
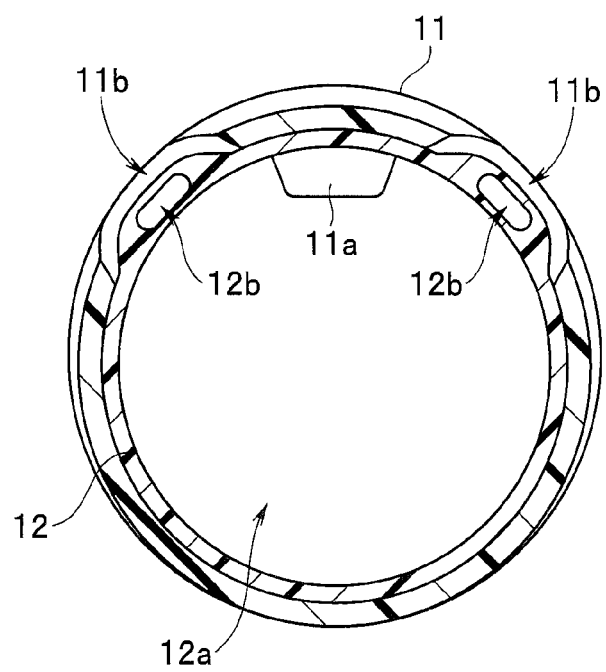
FIG. 7 is a sectional view (taken along a line [7]-[7] in FIG. 4) of a joint site of the distal end configuring member and the tube-shaped insertion portion in the endoscope cleaning sheath in FIG. 1.
Figure 8:
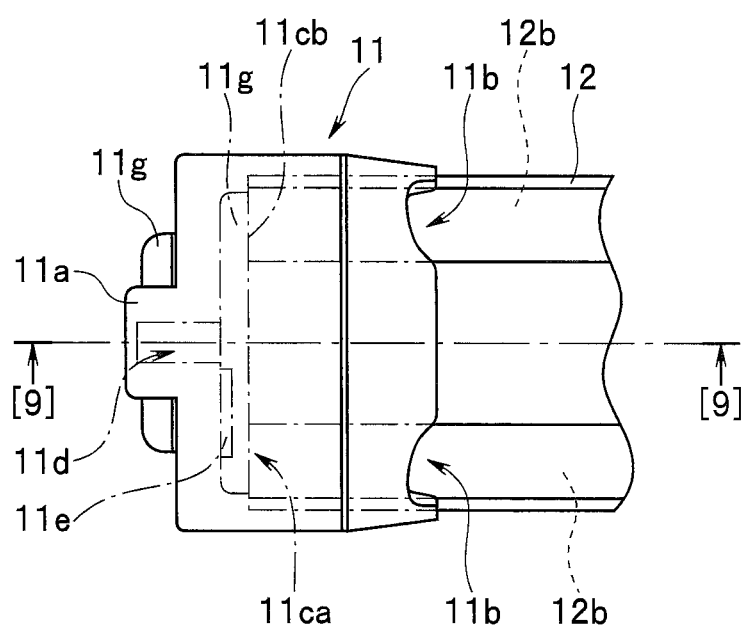
FIG. 8 is a top view seen from an arrow [8] direction in FIG. 4.

As shown in FIG. 5, FIG. 8 and the like, the above described channel 11c is formed so that a section is in a groove shape along a circumferential direction of the distal end configuring member 11. As shown in FIG. 8, one (a gas feeding side) of the above described two sub lumens 12b is provided connectively to a vicinity of one end portion of the channel 11c, and to a vicinity of the other end portion of the channel 11c, the other one (a liquid feeding side) of the above described two sub lumens 12b is provided connectively. Here, an opening at a side where the sub lumen 12b for gas feeding is connectively provided is called a gas feeding side opening, and is represented by a reference sign 11cb in FIG. 5, FIG. 8 and the like. Further, an opening at a side where the sub lumen 12b for liquid feeding is connectively provided is called a liquid feeding side opening, and is represented by a reference sign 11ca in FIG. 5, FIG. 8 and the like.

Further, a gas and a liquid that flow into the channel 11c join each other in a vicinity of a substantially central portion of the channel 11c. An opening 11da is formed in a vicinity of a joining portion. The opening 11da is formed at a proximal end side of the channel 11d which extends toward an axial direction front side (a distal end side) of the distal end configuring member 11. The channel 11d communicates with the above described spray nozzle 11a at a distal end side thereof.

Figure 9:
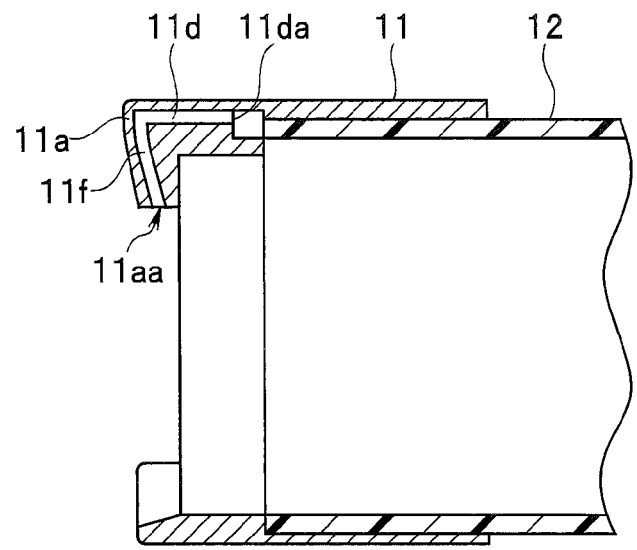
FIG. 9 is a sectional view taken along a line [9]-[9] in FIG. 8.

The above described spray nozzle 11a is formed integrally as a part of the above described distal end configuring member 11, and a distal end of the above described channel 11d is connectively provided at the spray nozzle 11a. As shown in FIG. 9, inside the spray nozzle 11a, a bent channel 11f connectively provided at the above described channel 11d is formed. The bent channel 11f is formed to be bent in a radial direction of the endoscope cleaning sheath 1 with respect to the above described channel 11d which is formed in the axial direction, and at a terminal end thereof, the ejection port 11aa is formed. Accordingly, the ejection port 11aa is formed to face the observation window, the illuminating window and the like (not illustrated) on the distal end face of the endoscope 2 which is inserted through and is disposed in the endoscope cleaning sheath 1.

By the configuration as above, the gas that flows from the gas feeding side opening 11cb at one end of the channel 11c into the same channel 11c, and the liquid that flows from the liquid feeding side opening 11ca at the other end of the channel 11c into the same channel 11c join each other and are mixed in a vicinity of a mixing portion opening 11da that is formed in a vicinity of the substantially central portion of the channel 11c. Subsequently, the mixed liquid which is mixed and atomized in the mixing site flows into the channel 11d from the mixing portion opening 11da, reaches the ejection port 11aa of the above described spray nozzle 11a through the same channel 11d, and is sprayed toward the observation window, the illuminating window and the like (not illustrated) on the distal end face of the endoscope 2 which is inserted through and is disposed in the endoscope cleaning sheath 1 from the same ejection port 11aa.

As above, in the distal end configuring member 11 of the present embodiment, a mixing site (a site in the vicinity of the mixing portion opening 11da) where the gas and the liquid mix, and the site (the ejection port 11aa of the spray nozzle 11a) where the atomized mixed liquid is sprayed outside are respectively formed at the sites separated via the channel 11d (see FIG. 9). In other words, a plane where the mixing site (the site in the vicinity of the mixing portion opening 11da) is disposed, and a plane where the spray site (the ejection port 11aa of the spray nozzle 11a) is disposed are formed by being separated in the axial direction of the endoscope cleaning sheath 1.

By adoption of the configuration as above, in the distal end configuring member 11 of the present embodiment, an ejecting direction of the fed gas that is ejected from the ejection port 11aa can be restrained from inclining at a time of a gas feeding action, and the gas feeding action to a predetermined direction can be reliably performed, with respect to the conventional configuration in which the mixing site and the spraying site are disposed on the same plane, for example. Further, in the configuration according to the distal end configuring member 11 of the present embodiment, the channel 11d is provided connectively to the spray nozzle 11a, and a spraying direction is defined by the bent channel 11f of the spray nozzle 11a. Therefore, an atomized mixed liquid can be reliably sprayed in the predetermined direction.

Further, as shown in FIG. 5, FIG. 8 and the like, inside the above described channel 11c, a wall-shaped protrusion 11e is formed in a space (namely, a space at a side where a liquid mainly flows, in the above described channel 11c) between a site in a vicinity of the liquid feeding side opening 11ca and a site in a vicinity of the above described mixing portion opening 11da. The wall-shaped protrusion 11e is formed along one wall surface of the above described channel 11c, for example (see FIG. 6). Generally, in the endoscope cleaning sheath of the mode as described above, when an operation of spraying the mixed liquid atomized by gas feeding and liquid feeding being performed is performed, and thereafter the spraying operation is stopped, a liquid that does not reach the ejection port of the spray nozzle sometimes remains in the channel at the liquid feeding side. Especially in the case of the channel configuration of the aforementioned mode, a vicinity of the joint site (the liquid feeding side opening 11ca) of the sub lumen 12b for liquid feeding and the channel 11c is a site where a direction of a flow of the liquid which is fed through the sub lumen 12b for liquid feeding changes. That is to say, the liquid which flows in the sub lumen 12b for liquid feeding has the direction of the flow changed by an angle of substantially 90 degrees immediately after the liquid flows into the channel 11c from the liquid feeding side opening 11ca. In the site like this, the liquid tends to accumulate when gas feeding and liquid feeding are stopped.

Here, if the next gas feeding operation is performed in a state in which the liquid remains in the channel, the remaining liquid is caught in the gas that flows into the channel 11c from the gas feeding side opening 11cb, flows in the channel 11c, moves to the channel 11d from the mixing portion opening 11da, and is finally ejected from the spray nozzle 11a. That is to say, the remaining liquid mixes into the fed gas and is sprayed although the gas feeding operation is being performed.

Therefore, in the distal end configuring member 11 of the present embodiment, the configuration is adopted, in which the above described wall-shaped protrusion 11e is formed at the predetermined site inside the channel 11c as described above, namely, the space between a site in the vicinity of the liquid feeding side opening 11ca and a site in the vicinity of the above described opening 11da, whereby the aforementioned problem, that is, the remaining liquid at the time of stoppage of the spraying operation is prevented from moving easily at the next time of the gas feeding operation. Namely, the above described wall-shaped protrusion 11e is formed in the channel at the liquid feeding side of the channel 11c, whereby a flow of the remaining liquid is inhibited. Thereby, such a configuration is made, that even if a gas feeding operation is performed in a state in which the remaining liquid exits inside the channel 11c, movement of the remaining liquid is inhibited, whereby the liquid does not mix into the fed gas, and gas feeding can be reliably performed.

As described above, the spray nozzle 11a is formed so that the mixed liquid ejected from the ejection port 11aa is sprayed toward the observation window, the illuminating window and the like (not illustrated) on the distal end face of the endoscope 2 which is inserted through and is disposed in the endoscope cleaning sheath 1. Accordingly, the mixed liquid which is sprayed toward the observation window, the illuminating window and the like (not illustrated) on the distal end face of the endoscope 2 is separated into drops on the outer surfaces of the above descried respective windows and cleans the outer surfaces, and the liquid after cleaning is likely to drip along an outer circumferential side surface and the like of the distal end configuring member 11 of the endoscope cleaning sheath 1, go around to the front surface side of the endoscope 2 again, accumulate in the vicinity of the ejection port 11 as of the spray nozzle 11a.

Figure 10:
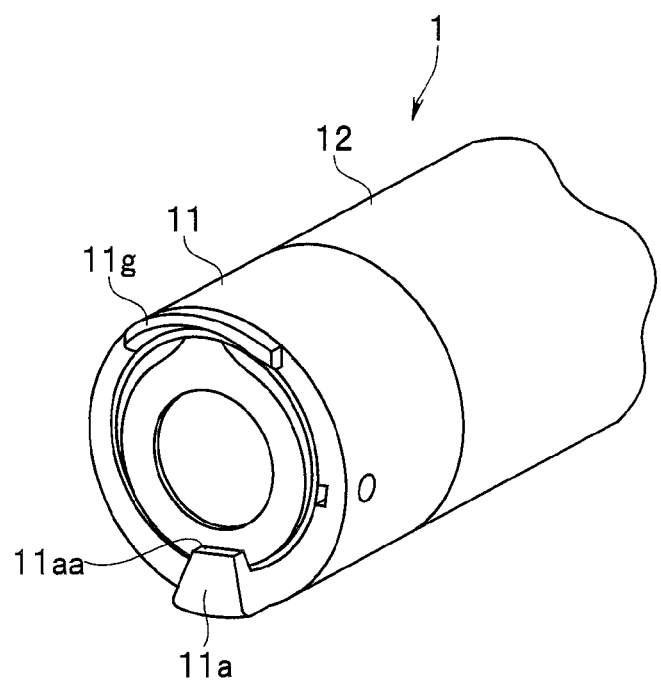
FIG. 10 is an essential part enlarged perspective view showing a front surface side by enlarging the distal end site of the endoscope cleaning sheath in FIG. 1.

Therefore, in the distal end configuring member 11 of the present embodiment, an arc-shaped wall portion 11g is formed at a site that is a part of an outer circumferential edge portion of the front surface side of the distal end configuring member 11 and faces the ejection port 11aa of the above described spray nozzle 11a, as shown in FIG. 10 and the like. The arc-shaped wall portion 11g is provided, whereby the liquid after being sprayed from the ejection port 11aa of the above described spray nozzle 11a and cleaning the outer surfaces of the above described respective windows of the above described endoscope 2 is restrained from flowing out to the outer circumferential side surface and the like of the distal end configuring member 11, and the liquid after cleaning is configured to be scattered mainly forward of the endoscope cleaning sheath 1. Accordingly, the liquid after the cleaning can be restrained from making the outer surfaces of the above described respective windows dirty by going around to the front surface side of the endoscope 2 again, and from accumulating in the vicinity of the ejection port 11aa of the spray nozzle 11a.

Furthermore, the mixed liquid after being sprayed tends to accumulate in the vicinity of the ejection port 11aa of the spray nozzle 11a by adhering and being separated into drops. Therefore, in the distal end configuring member 11 of the present embodiment, water-repellent coating treatment is applied to the vicinity of the ejection port 11aa of the spray nozzle 11a. The surface treatment like this is applied to the site, whereby the liquid which adheres and is separated into drops quickly runs down, and thereby an effect of inhibiting the liquid from accumulating in the site is provided.

Further, as for an external shape of the distal end configuring member 11 of the present embodiment, an outside diameter at a proximal end side is formed into a shape substantially similar to an outer circumferential shape of the above described tube-shaped insertion portion 12, as shown in FIG. 4 and the like. The portion is called a proximal end portion 11x in the distal end configuring member 11. Further, a distal end side is formed into a substantially circular shape having an outside diameter equal to or larger than a maximum outside diameter of the above described proximal end portion 11x. The portion is called a distal end portion 11y. A portion between the above described proximal end portion 11x and the above described distal end portion 11y is formed in such a manner that an outside diameter changes continuously from the above described proximal end portion 11x to the above described distal end portion 11y. The portion is called a continuous portion 11z. Further, cutout portions 11b are formed at respective sites that are sites ranging from the aforementioned proximal end portion 11x to an intermediate portion of the aforementioned continuous portion 11z, and correspond to the above described plurality of convex portions of the above described tube-shaped insertion portion 12.

Figure 11:
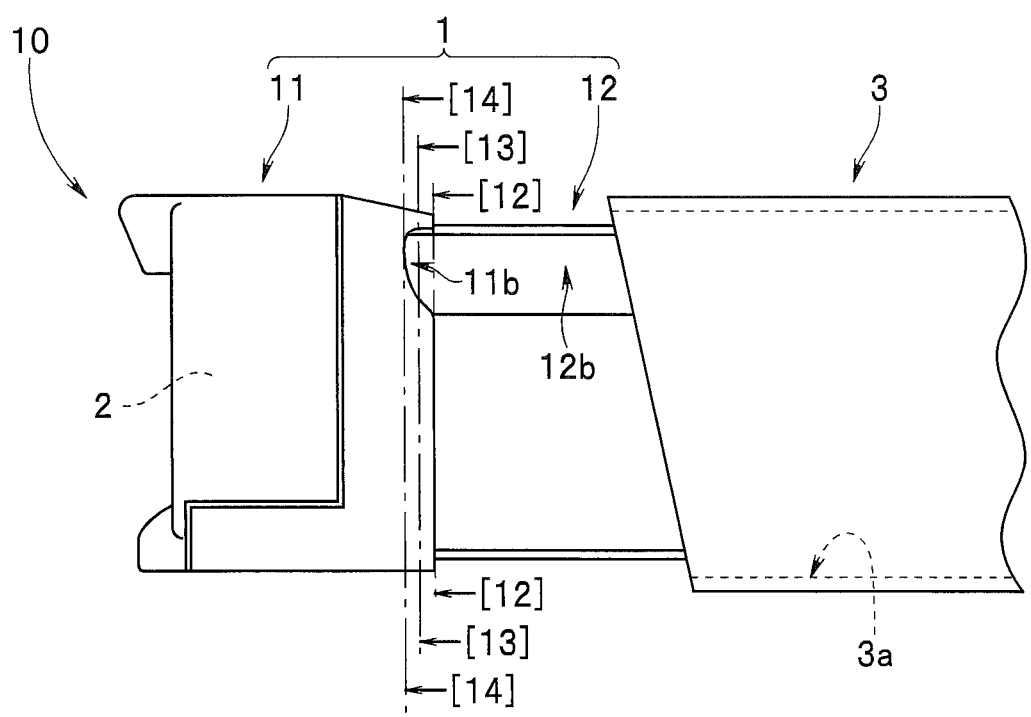
FIG. 11 is a side view showing a state in which the endoscope cleaning sheath in FIG. 1 is inserted through a trocar and a most distal end site is protruded forward.

That is to say, in the distal end configuring member 11, two of the cutout portions 11b that are formed into shapes that are cut out into concave shapes, substantially arc shapes or rectangular shapes in an axial direction from a circumferential edge portion of the above described proximal end portion 11x are formed at respective sites that are parts of a circumferential edge portion at a proximal end side (the proximal end portion 11x) in the axial direction thereof, namely, a side where the tube-shaped insertion portion 12 is joined, and are raised in a radial direction with the two sub lumens 12b of the tube-shaped insertion portion 12 disposed respectively therein. That is to say, the two concave cutout portions 11b are formed in the sites corresponding to the respective two sub lumens 12b. The two concave cutout portions 11b are provided, whereby a sectional shape in the vicinity of the edge portion at the proximal end side in the axial direction of the above described distal end configuring member 11 is formed into a substantially circular shape as shown in FIG. 11 to FIG. 14. Further, as shown in FIG. 11, end surfaces in vicinities of the two concave cutout portions 11b (only one is illustrated in FIG. 11) are formed to be gradual upward inclined surfaces from an edge portion at the proximal end side in the axial direction of the distal end configuring member 11 to a front.

An operation at a time of use of the endoscope cleaning sheath 1 including the distal end configuring member 11 of the present embodiment including the configuration as above will be described as follows.

First, as shown in FIG. 1, the endoscope insertion portion 22 of the above described endoscope 2 is inserted to the main lumen 12a of the tube-shaped insertion portion 12 from the opening 13a of the operation portion 13 of the above described endoscope cleaning sheath 1. The endoscope cleaning sheath 1 in this state is inserted through and is disposed in the trocar 3 which is a tubular member. In this state, observation of an inside of a body cavity and the like using the endoscope 2 can be performed. In this case, the endoscope cleaning sheath 1 through which the endoscope 2 is inserted is sometimes used in a state in which a distal end portion of the endoscope cleaning sheath 1 is protruded from the distal end of the trocar 3, as shown in FIG. 11. When the endoscope cleaning sheath 1 which is inserted through the trocar 3 is removed from the state, a most distal end portion of the trocar 3 abuts on the proximal end side of the distal end configuring member 11 of the endoscope cleaning sheath 1 first. The state at this time is as shown in FIG. 12.

Figure 12:
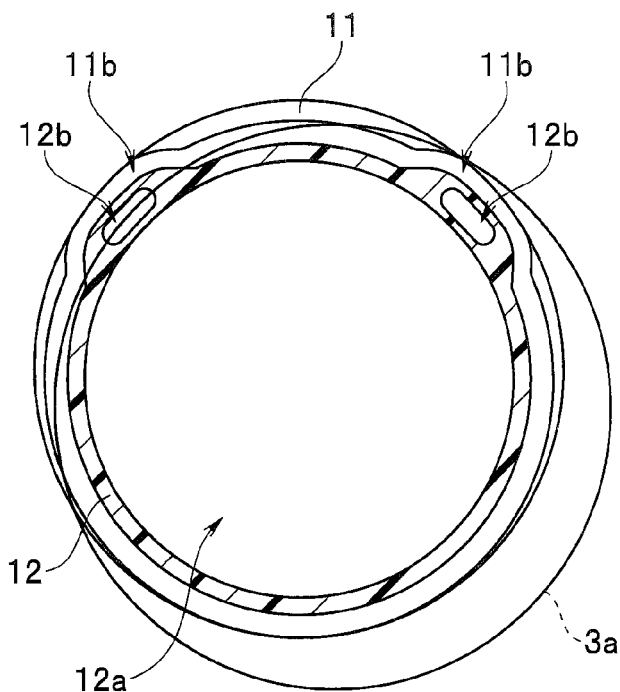
FIG. 12 is a sectional view taken along a line [12]-[12] in FIG. 11.
Figure 13:
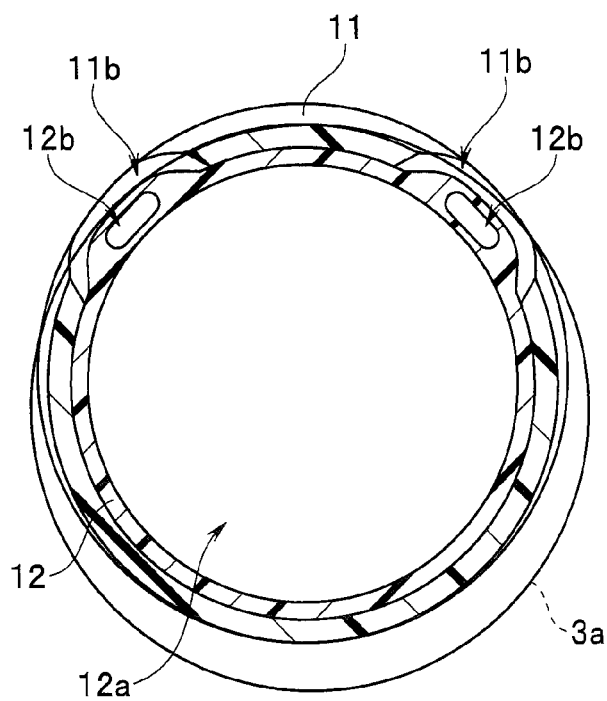
FIG. 13 is a sectional view taken along a line [13]-[13] in FIG. 11.
Figure 14:
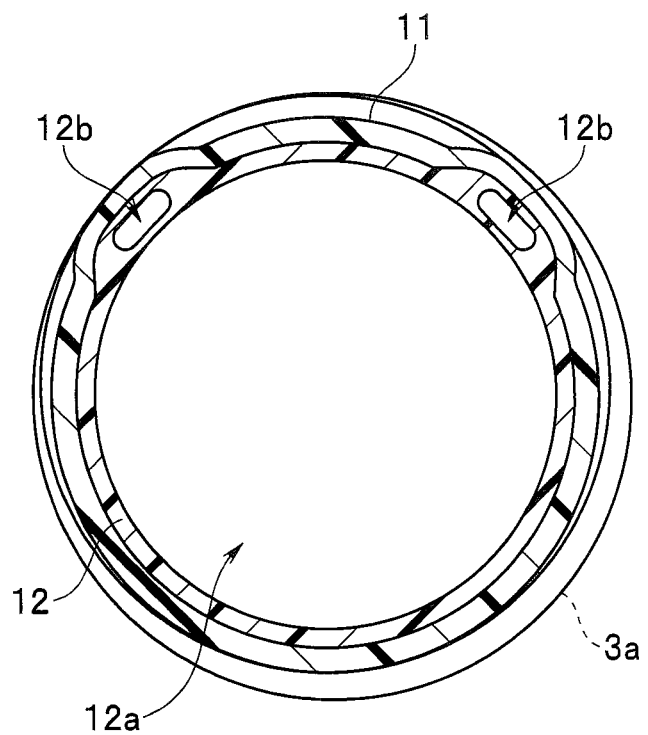
FIG. 14 is a sectional view taken along a line [14]-[14] in FIG. 11.

The state shown in FIG. 12 shows a state in which an inner wall surface 3a of the trocar 3 is caused to be along one of the two sub lumens 12b when the endoscope cleaning sheath 1 is removed from the trocar 3. When the state like this is brought about, the endoscope cleaning sheath 1 advances in a removing direction while the inner wall surface 3a of the trocar 3 remains in a form of crushing the conduit of the sub lumen 12b from outside. Subsequently, as shown in FIG. 12, one of the two concave cutout portions 11b at the proximal side of the distal end configuring member 11 of the endoscope cleaning sheath 1 abuts on the most distal end portion of the trocar 3. That is to say, the most distal end portion of the trocar 3 reaches the proximal end portion 11x (see FIG. 4) of the distal end configuring member 11. At this time, the edge portion at the proximal end side of the distal end configuring member 11 advances in the removing direction smoothly without being caught by the most distal end portion of the trocar 3, because the end surface of the concave cutout portion 11b is formed to be the gradual upward inclined surface from the edge portion of the proximal end side in the axial direction of the distal end configuring member 11 to the front, as described above. That is to say, the most distal end portion of the trocar 3 advances to the distal end side from the proximal end side of the concave cutout portion 11b. Here, in the concave cutout portion 11b, a boundary portion of the distal end configuring member 11 and the tube-shaped insertion portion 12 extends inside in an inlet shape (a substantially arc shape) toward the distal end side from the proximal end portion 11x of the distal end configuring member 11b. Accordingly, the most distal end portion of the trocar 3 cannot reach a boundary portion of the concave cutout portion 11b and the tube-shaped insertion portion 12. Further, an outside diameter of the continuous portion 11z (see FIG. 4) becomes larger toward the distal end side, and therefore, as the distal end portion of the trocar 3 advances to the distal end side of the concave cutout portion 11b, the distal end portion of the trocar 3 is moved farther away in an outside diameter direction from the above described boundary portion. Accordingly, when removal of the endoscope cleaning sheath 1 is continued as it is, the above described edge portion inclined surface at the proximal end side of the distal end configuring member 11 is smoothly removed while sliding on an inner wall surface of the trocar 3 from the state shown in FIG. 13 to the state shown in FIG. 14. Subsequently, after the state shown in FIG. 14, the endoscope cleaning sheath 1 can be removed smoothly while an outer circumferential face of the distal end configuring member 11 is slid to the inner wall surface of the trocar 3.

As described above, according to the above described one embodiment, the distal end configuring member 11 in the medical instrument such as the endoscope cleaning sheath 1 is formed by having the proximal end portion 11x having the inside diameter capable of receiving the distal end of the tube-shaped insertion portion 12 having the shape including the substantially circular outer circumferential portion as a whole, and the convex portions that are formed at the outer circumferential portion as the outer circumferential shape, and has the outside diameter formed into the shape substantially similar to the outer circumferential shape of the above described tube-shaped insertion portion 12, the distal end portion 11y in the substantially circular shape having the outside diameter equal to or larger than the maximum outside diameter of the above described proximal end portion 11x, the continuous portion 11z which is provided between the above described proximal end portion 11x and the above described distal end portion 11y, and has the outside diameter changing continuously from the above described proximal end portion 11x to the above described distal end portion 11y, and the cutout portions 11b which are formed at the sites which are the sites ranging from the above described proximal end portion 11x to the intermediate portion of the above described continuous portion 11z and correspond to the above described convex portions (the sub lumens 12b) of the above described tube-shaped insertion portion 12.

The distal end configuring member 11 which is configured as above is adopted in the endoscope cleaning sheath 1 which is the medical instrument, whereby when the endoscope cleaning sheath 1 which is inserted through the trocar 3 is removed, the distal end configuring member 11 of the endoscope cleaning sheath 1 can be restrained from being caught by the most distal end portion of the trocar 3. Accordingly, insertion and removal of the endoscope cleaning sheath 1 (the medical instrument) can be always performed smoothly.

Figure 15:
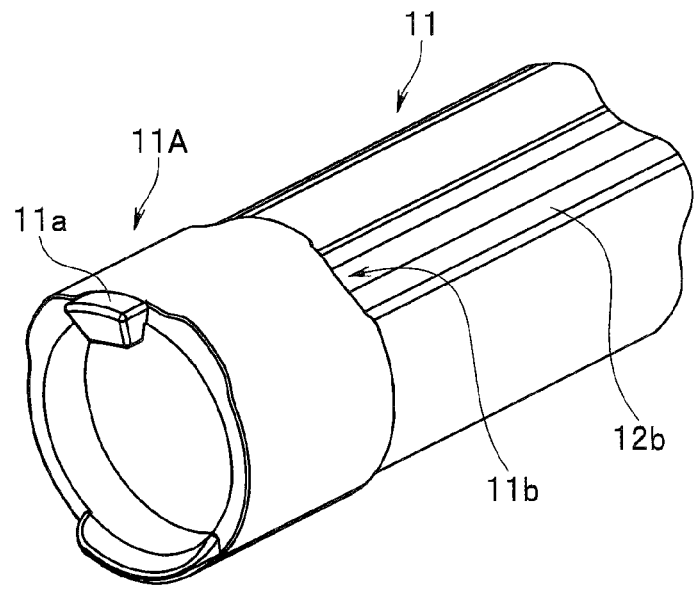
FIG. 15 is a perspective view showing a modification of a distal end configuring member of one embodiment of the present invention, and showing only a part (a distal end portion) of an endoscope cleaning sheath including the distal end configuring member.
Figure 16:
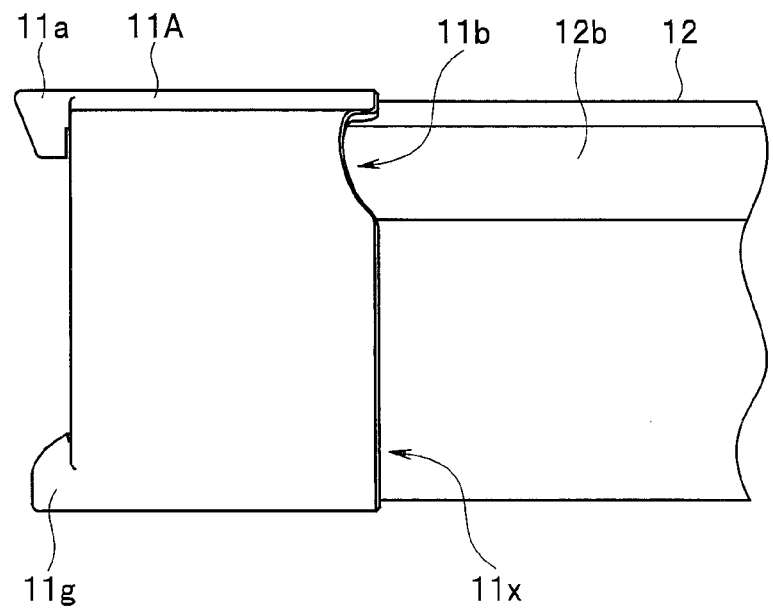
FIG. 16 is a side view showing a part (the distal end portion) of the endoscope cleaning sheath in FIG. 15.

Further, as a modification of the distal end configuring member 11 shown in the aforementioned embodiment, a mode shown as follows may be adopted. FIG. 15 and FIG. 16 are views showing a part (a distal end portion) of an endoscope cleaning sheath including the distal end configuring member, which is the modification of the distal end configuring member of the one embodiment of the present invention. Of the drawings, FIG. 15 is a perspective view showing a schematic configuration of the distal end portion in the endoscope cleaning sheath. FIG. 16 is a side view of the same site.

A basic configuration of a distal end configuring member 11A of the present modification includes a configuration substantially similar to the configuration of the distal end configuring member 11 shown in the aforementioned one embodiment, and only a part of the shape differs. Accordingly, the same components as in the aforementioned one embodiment will be assigned with the same reference signs, and explanation thereof will be omitted. Only different portions will be described in detail as follows.

In the distal end configuring member 11 in the aforementioned one embodiment, the end faces in the vicinities of the two concave cutout portions 11b are formed to be the gradual upward inclined surfaces toward the front from the edge portion at the proximal end side in the axial direction of the distal end configuring member 11. That is to say, the end faces are formed by being provided with the above described continuous portions 11z (see FIG. 4).

In contrast with the above, in the distal end configuring member 11A in the present modification, the end faces are formed without the above described inclined surfaces being provided, as shown in FIG. 15 and FIG. 16. That is to say, the distal end configuring member 11A of the present modification is in a substantially cylindrical shape as a whole, and is formed to be a cylindrical shape with the substantially same outside diameter from the proximal end portion 11x to the distal end portion. In the distal end configuring member 11A, the two concave cutout portions 11b are provided similarly to the aforementioned one embodiment.

In the endoscope sheath to which the distal end configuring member 11A shown in the above described modification which is configured as above, in the portion of the concave cutout portion 11b, the boundary portion of the distal end configuring member 11A and the tube-shaped insertion portion 12 is in a shape going inward to the distal end side from the proximal end portion 11x of the distal end configuring member 11A in an inlet shape, and therefore, the most distal end portion of the trocar 3 cannot reach the boundary portion of the concave cutout portion 11b and the tube-shaped insertion portion 12. Accordingly, an effect totally similar to the effect of the aforementioned one embodiment can be obtained.

Note that the present invention is not limited to the aforementioned embodiment, and various modifications and applications can be carried out within the range without departing from the gist of the present invention, as a matter of course. Furthermore, the above described embodiment includes the inventions at various stages, and various inventions can be extracted by proper combinations in the plurality of components which are disclosed. For example, even when several components are deleted from all the components shown in the above described one embodiment, if the problem to be solved by the invention can be solved, and the effect of the invention can be obtained, the configuration from which the components are deleted can be extracted as the invention.

What is claimed is:

1. A distal end configuring member of a medical instrument comprising:
   a proximal end portion including,
      an inner circumferential face capable of receiving a distal end portion of a tube-shaped member, the tube shaped member having a shape including a substantially circular outer circumferential portion and a convex portion formed so as to be raised in a radial direction at the outer circumferential portion as an outer circumferential shape, and the inner circumferential face being formed into a shape substantially similar to the outer circumferential shape of the tube shaped member;
      an outer circumferential face formed into a shape substantially similar to the shape of the inner circumferential face, and
      a concave portion formed at a site corresponding to the convex portion, the concave portion being cut out from a proximal end side toward a distal end side in a concave shape, the concave portion being formed from the outer circumferential face to reach the inner circumferential face at the site corresponding to the convex portion; and
   a distal end portion in a substantially cylindrical shape having an outside diameter that is equal to or larger than a maximum outside diameter of the proximal end portion.

2. The distal end configuring member of a medical instrument according to claim 1, wherein the convex portion is in a substantially arc shape.

3. The distal end configuring member of a medical instrument according to claim 1, wherein the cutout portion is cut out in an arc shape or a rectangular shape from the proximal end portion.

4. The distal end configuring member of a medical instrument according to claim 1, further comprising:
   a continuous portion in which an outside diameter continuously changes from the proximal end portion to the distal end portion, between the proximal end portion and the distal end portion,
   wherein the cutout portion is formed in a site that is a site ranging from the proximal end portion to an intermediate portion of the continuous portion, and corresponds to the convex portion.

5. The distal end configuring member of a medical instrument according to claim 1, further comprising:
   a spray nozzle disposed at the distal end portion that sprays an atomized mixed liquid of a gas and a liquid.

6. An endoscope system comprising:
   an endoscope cleaning sheath comprising:
      a tube-shaped insertion portion having a shape including a substantially circular outer circumferential portion and a convex portion formed at the outer circumferential portion, as an outer circumferential shape, and
      a distal end configuring member formed by including a proximal end portion having an inside diameter capable of receiving the tube-shaped insertion portion, and having an outside diameter formed into a shape substantially similar to the outer circumferential shape, a distal end portion in a substantially circular shape having an outside diameter equal to or larger than a maximum outside diameter of the proximal end portion, a cutout portion that is formed in a site corresponding to the convex portion and is in a shape which is cut out from the proximal end portion to the distal end portion, and a spray nozzle that sprays an atomized mixed liquid of a gas and a liquid; and
   a tubular member inserted through which the endoscope cleaning sheath.

7. An insertion portion of a medical instrument comprising:
   a tube portion having an outer circumferential shape including a substantially circular outer circumferential portion and a convex portion formed so as to be raised in a radial direction at the outer circumferential portion; and a distal end configuring member into which a distal end portion of the tube portion is inserted, the distal end configuring member including:
   at a proximal end portion thereof, an inner circumferential face formed into a shape substantially similar to the outer circumferential shape of the tube portion;
   an outer circumferential face,
   a concave portion formed at a site corresponding to the convex portion, the concave portion being cut out from a proximal end side toward a distal end side in a concave shape, the concave portion being formed from the outer circumferential face to reach the inner circumferential face at the site corresponding to the convex portion, and
a distal end portion in a substantially cylindrical shape having an outside diameter that is equal to or larger than a maximum outside diameter of the proximal end portion.

\* \* \* \* \*